United States Patent
Xu et al.

(10) Patent No.: US 6,363,163 B1
(45) Date of Patent: *Mar. 26, 2002

(54) METHOD AND SYSTEM FOR THE AUTOMATED TEMPORAL SUBTRACTION OF MEDICAL IMAGES

(75) Inventors: Xin-Wei Xu, Darien; Kunio Doi, Willowbrook, both of IL (US)

(73) Assignee: Arch Development Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,468

(22) Filed: Feb. 23, 1998

(51) Int. Cl.[7] .................................................. G06K 9/00
(52) U.S. Cl. ........................ 382/130; 382/131; 382/154; 382/294
(58) Field of Search ................................ 382/128, 130, 382/131, 154, 132, 294; 128/922, 320; 378/901; 250/363.04

(56) References Cited

U.S. PATENT DOCUMENTS

| | | | |
|---|---|---|---|
| 5,319,549 A | * 6/1994 | Katsuragawa et al. | 129/922 |
| 5,359,513 A | * 10/1994 | Kano et al. | 382/128 |
| 5,633,951 A | * 5/1997 | Moshfeghi | 382/154 |
| 5,787,899 A | * 8/1998 | Edwards et al. | 128/916 |
| 5,839,440 A | * 11/1998 | Liou et al. | 128/654 |
| 5,881,124 A | * 3/1999 | Giger et al. | 378/901 |

OTHER PUBLICATIONS

Hasegawa "Automated extraction of lung cancer lesions from multislice chest CT images by using three–dimensional image processing" Systems and Computers in Japan vol. 25, No. 11, p. 68–77, Oct. 1994.*

Chapnick et al. "Techniques for multimodality image registration" Bioengineering conference, 1993., Proc. of the 1993 IEEE Nineteenth Annual Northeast, p. 221–222, Mar. 1993.*

Ettinger et al. "Automatic registration for multiple sclerosis change detection" Proc. fo the IEEE Workshop on Biomedical Image Analysis 1994, Jun. 1994.*

Moshfeghi et al. "Three–Dimensional Elastic Matching of Volumes" IEEE Transactions on Image Processing vol. 3 No. 2 pp. 128–138, Mar. 1994.*

Hasegawa "Automated extraction of lung cancer lesions from multislice chest CT images by using three–dimensional image processing" Systems and Computers in Japan vol. 25, No. 11, p. 68–77, Oct. 1994.*

Chapnick et al. "Techniques for multimodality image registration" Bioengineering conference, 1993., Proc. of the 1993 IEEE Nineteenth Annual Northeast, p. 221–222, Mar. 1993.*

* cited by examiner

*Primary Examiner*—Amelia M. Au
*Assistant Examiner*—Jingge Wu
(74) *Attorney, Agent, or Firm*—Oblon, Spivak, McClelland, Maier & Neustadt, P.C.

(57) ABSTRACT

Method and system for the detection of interval change in medical images. Three dimensional images, such as previous and current section images in CT scans, are obtained. An anatomic feature, such as the lungs, is used to select sections containing lung by a gray-level thresholding technique. The section correspondence between the current and previous scans is determined automatically. The initial registration of the corresponding sections in the two scans is achieved by a rotation correction and a cross-correlation technique. A more accurate registration between the corresponding current and previous section images is achieved by local matching. A nonlinear warping process which is also based on the cross-correlation technique is applied to the previous image to yield a warped image after the matching. The final subtracted section images were derived by subtracting of the previous section images from the corresponding current section images. Interval changes such as a change in tumor size and a newly developed pleural effusion are enhanced significantly.

59 Claims, 21 Drawing Sheets

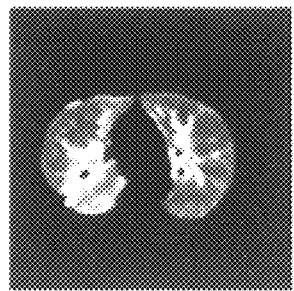
FIG.4A
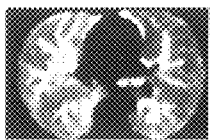 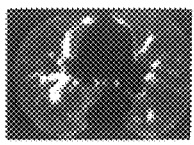 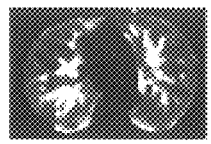 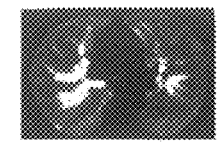 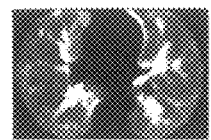
FIG.4B     FIG.4C     FIG.4D     FIG.4E     FIG.4F

METHOD AND SYSTEM FOR THE AUTOMATED TEMPORAL SUBTRACTION OF MEDICAL IMAGES

CROSS-REFERENCE TO RELATED APPLICATIONS

The present is related to automated techniques for automated detection of abnormalities in digital images, for example as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; as well as U.S. applications Ser. Nos. 08/158,388; 08/173,935; 08/220,917; 08/398,307; 08/428,867; 08/523,210; 08/536,149; 08/536,450; 08/515,798; 08/562,188; 08/562,087; 08/757,611; 08/758,438; 08/900,188; 08/900,189; 08/900,191; 08/900,192; 08/900,361; 08/900,362; 08/979,623; 08/979,639; 08/982,282; 09/0285/8; and Ser. No. 09/027685, each of which are incorporated herein by reference in their entirety. Of these patents and applications, U.S. Pat. No. 5,319,549 and Ser. No. 08/900,362 are of particular interest.

STATEMENT REGARDING FEDERALLY SPONSORED RESEARCH

The present invention was made in part with U.S. Government support under grant numbers CA 62625 and CA 64370 (National Institutes of Health) and DAMD 71-96-6228 (U.S. Army). The U.S. Government has certain rights in the invention.

BACKGROUND OF THE INVENTION

1. Field of the Invention

The present invention is related to temporal analysis of medical images and, in particular, to the analysis of computed tomographic images using automated temporal subtraction.

2. Discussion of the Background

The application of a temporal subtraction technique to radiographic images such as chest images can significantly enhance some subtle interval changes existing in sequentially obtained images which might be missed by radiologists. These interval changes may be very important in enabling radiologists to detect some diseases, such as early lung cancer, or to assess the effects of treatment on known lesions. Difazio et al., in Digital chest radiography: Effect of temporal subtraction images on detection accuracy, Radiology, 202:447–452 (1997) reported that the use of the temporal subtraction technique for sequential chest images can significantly increase radiologists' diagnostic accuracy in identifying interval changes.

When radiologists interpret a thoracic computed tomography (CT) scan of a patient, they commonly view it side by side with the most recent previous scan of the same patient. Such comparison readings also help radiologists to identify interval changes or to assess the effects of treatment on known lesions between two consecutive thoracic CT examinations. However, it is difficult and time-consuming for radiologists to compare current and previous (temporally sequential) thoracic CT scans to identify new findings or to assess the effects of treatments on known lesions, because this requires a systematic visual search and correlation of a large number of images (sections) in both current and previous scans. Generally, more than 25 section images were reconstructed from a thoracic CT scan with a section thickness of 10 mm. The number of section images may be much higher when a high-resolution scan (section thickness of 3 mm) is required.

Viewing several images can be difficult because of variations in the images. For example, the positioning of the patient may be different at the various times the images are produced. Patient breathing and cardiac pulsation can also produce variances in the images. It is important to be able to register images to detect interval changes where corresponding features in the images can be subtracted from each other.

The techniques for temporal subtraction, such as described in U.S. Pat. No. 5,319,549, have only been applied to two-dimensional imaging. These techniques register and subtract two-dimensional images, such as chest radiographs.

SUMMARY OF THE INVENTION

It is an object of the present invention to provide improved automated temporal subtraction of images.

A second object of the invention is to enhance interval changes in images.

A further object of the present invention to perform automated temporal subtraction for three-dimensional scanning.

Another object of the present invention is to perform automated temporal subtraction using matching images in the direction of scanning.

A still further objection of the invention is to three-dimensionally match two images and two-dimensionally match corresponding sections of the two images.

These and other objects of the invention are achieved by a method, system and computer program product for detecting interval change in images. In the method according to the invention, first and second three-dimensional images of a subject are obtained. The first and second images are typically current and previous images of a subject. The first and second images are matched. The first image is non-linearly warped to produce a warped image and the warped image is subtracted from the second image. The subtraction can produce and/or enhance interval changes in the first and second images.

A portion of the first image may be selected using an anatomic feature in the first image. A portion of the second image may be selected using the same anatomic feature. Relative areas of the anatomic feature in the first and second images may be determined. The portions of the first and second images may be selected using the relative areas determined in the first and second images, respectively.

Determining the relative areas may be done by thresholding the first and second images to obtain corresponding regions in the first and second images. An area of each of these regions is determined and the relative areas are then determined as a ratio of an area of these regions to remaining areas in the images.

The matching of the images may be done by comparing the first and second relative areas. The matching may also be done by determining a first relationship of the area of the anatomic feature in the first and second images. Averages of the relationships of the areas can then be determined and sections of the first and second images corresponding to the averages can be selected.

It is also possible to select one section in the first image and a number of sections adjacent to that section. These sections are compared to one section selected in the second image. One of the sections selected in the first image is then matched to the section in the second image. Remaining sections in the first image may then be matched in a one-to-one manner to remaining sections and the second image.

Cross-correlation may be used in matching the images. The matching may also consist of initially matching the first image to the second image and then locally matching the first image to the second image. The initial matching may consist of determining whether the first image is rotated and correcting the rotation, and determining vertical and horizontal shifts of the first image relative to the second image. Cross-correlation may use the vertical and horizontal shifts in matching the first and second images.

The local matching may consist of selecting regions of interest in the first and second images and determining horizontal and vertical shifts of regions of interest in the first image relative to regions of interest in the second image. The horizontal and vertical shifts may then be curve-fitted and the used in a warping process to warp the first image. The warped image may be subtracted from the second image to produce a subtracted image.

The method may also include analyzing the registration of the subtracted images. If the registration is inadequate, the image data may be retrieved and the current image may be reconstructed at a different reconstruction starting point. The analysis of the registration may be performed using histogram analysis.

The method may be advantageously applied to computed tomography (CT) scanning. In this case, the three-dimensional matching consists of matching the current and previous scans while the two-dimensional matching consists of matching the corresponding sections of the current and previous CT scans.

The invention may also be implemented in the form of a computer program product comprising a computer storage medium and a computer program code mechanism embedded in the computer storage medium. Code devices are then configured to implement various steps in detecting interval change.

These objects are also achieved by an interval change detecting system having at least one of a three-dimensional image storage device and a three-dimensional image acquisition device. A scanning direction image matching device is connected to one of the acquisition device and storage device. The system may also include a two-dimensional image matching device and a relative area determination circuit. Invention may further include a local matching circuit, a warping circuit and a cross correlation circuit. It is also possible that the system contains a registration analysis circuit which may consist of a histogram analysis circuit, an image data retrieval circuit and an image data reconstruction circuit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4A is an example of a segmented, low-resolution image from the mid-section image of a current CT scan and FIGS. 4B–4F are examples of ROI images obtained from the previous scan around the mid-section, respectively;

DESCRIPTION OF THE PREFERRED EMBODIMENTS

Figure 1:
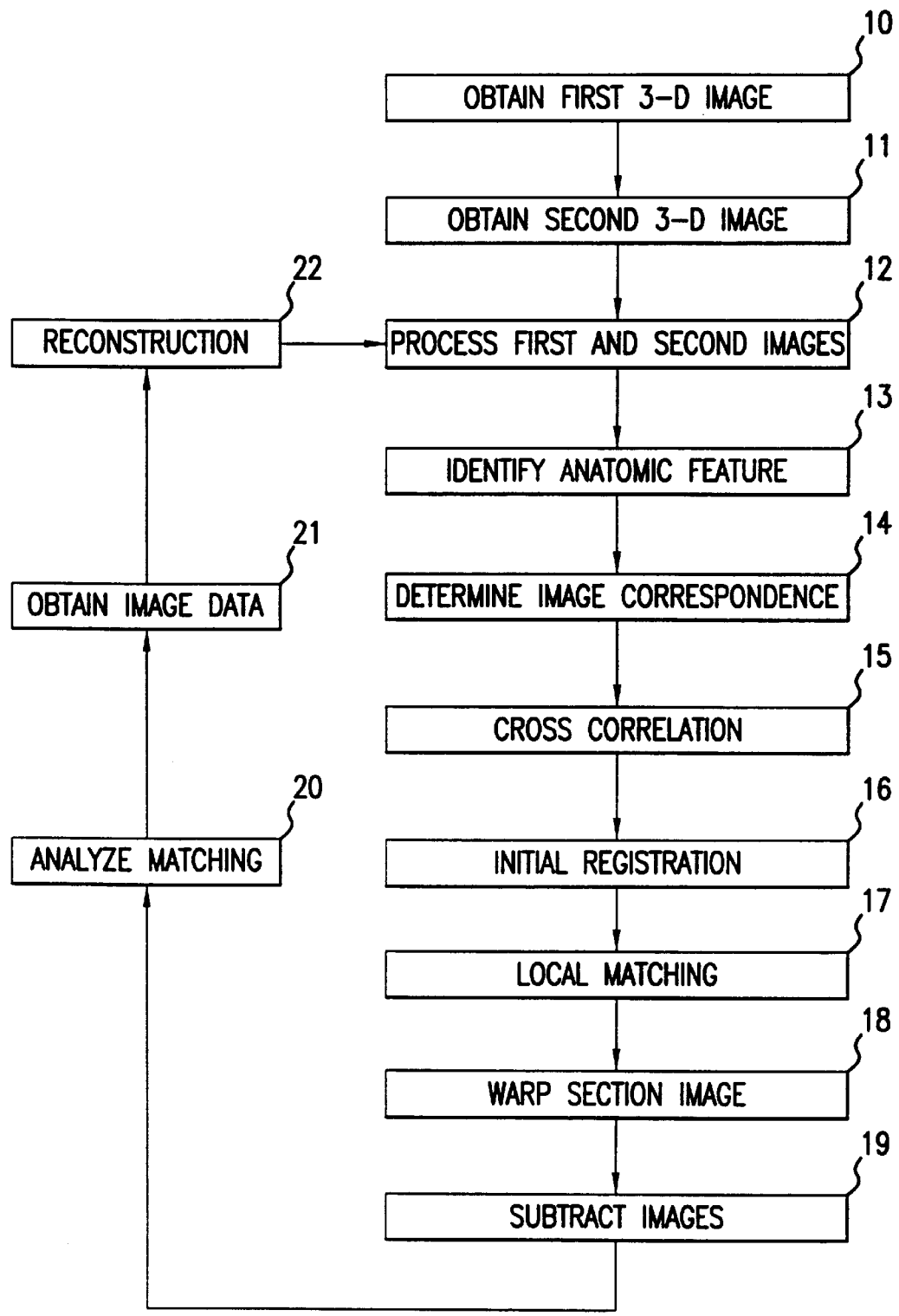
FIG. 1 is a diagram of an embodiment of the method according to the invention.

With reference to the drawings, particularly FIG. 1, a first embodiment of the method according to the invention will be described. First (step 10) and second (step 11) three-dimensional images of a patient are obtained. The first and second images typically correspond to current and previous images of the same subject. The first and second images may also be two previous images of the same subject, where interval changes between the two images are desired. As an example of the invention, thoracic helical computed tomography (CT) scans of patients are obtained from a CT scanner, such as a GE HiSpeed CT/i. In CT scanning the first and second images are commonly referred to as current and previous scan. The scans are reconstructed from the image data acquired by the scanner. However, the invention is not limited to CT images. Other types of three-dimensional images, such as MRI images, may be used. The scanning pitch and section thickness for generating the CT images were 1 and 10 mm, respectively. Other values for these parameters may also be selected.

The images may be obtained directly from a scanner or may be obtained from a storage device. Typically the previous section images are from an earlier scan and have been stored. It is also not required that the images are obtained on the same or the same type of scanner. Further, the method according to the invention can also use the acquisition data (step 21) of the scans and then reconstruct the images (step 22) before further processing, which is also described in more detail below.

In this example, the reconstructed digital section images (with DICOM header) was used. The matrix size of each reconstructed section image was 512×512 pixels. The pixel size of the section images can vary because of the different field of view (FOV) used for reconstruction in the clinical environment. The FOV for the reconstruction used in a clinical environment can vary from 29 to 42 cm. The maximum FOV allowed for reconstruction is 48 cm for the GE scanners used. In this case (including the current and previous scans), a correction factor should be applied for the FOV to all of the section images to ensure a uniform pixel size for every section image. The gray scale of the section images was 12 bits (pixel values from 0 to 4095), which corresponds to Hounsfield units (HU) of −1023 to 3072. Notice that air, water, and bone correspond to HU of −1000, 0, and 1000, respectively. In consideration of computer storage and CPU time, it is sometimes desirable to reduce the matrix size and gray scale of the thoracic CT section images to, for example, 256×256 pixels and 10 bits, respectively.

Figure 2A:
FIGS. 2A and 2B are section images of a current thoracic CT examination by helical scanning and section images of a previous thoracic CT examination of the same patient, respectively.
Figure 2B:

A scan for a thoracic CT examination can include a large number of section images (each with 10 mm thickness, in this example) which extend from approximately the neck of the patient down to the lower abdomen, as shown in FIGS. 2A and 2B. An interval change is usually detected by comparing anatomic features in the previous and current scans. To demonstrate the invention, the lungs were chosen as the anatomic feature in the images to be compared. However, the method is applicable to other features in the image, particularly solid organs such as the liver and kidney, or to bone and enhanced vessels.

Two pre-processing steps, i.e., segmentation of the anatomic feature and Gaussian filtering, are applied in step 12 to the first and second images. In the example, the lungs are segmented from selected sections from both the current and previous scans. The lung segmentation was achieved by use of a gray-level thresholding technique. The CT images are digital gray-scale images having a plurality of pixels (i.e, 512×512). The gray levels of the lungs corresponded generally to HU of −900 to −400. With the gray-level thresholding technique, pixels with HU above −400 and below −900 were eliminated to provide the lung area. The lung area may be approximated by a rectangle. The rectangle may be determined using horizontal and vertical profiling to detect the upper, lower and side lung edges based upon changes in pixel values. A 9×9 smooth Gaussian filter was employed to blur the vessel structures inside the lungs.

In step 13 the portions of the images that contain the anatomic feature are identified. The portions of the images corresponding to the anatomic feature of interest, the lungs in this example, will be referred to as lung sections. For the CT images shown in FIGS. 2A and 2B, the lung sections are from section #5 to #24 and section #4 to #24, respectively. To select the lung sections from a thoracic scan, a parameter for each section in the scan is calculated, namely, the relative lung area. Here, relative lung area was defined by the ratio of the number of pixels in the section image with HU from approximately −900 to −400 to the number of remaining pixels in that section image. As mentioned above, the pixels with HU from approximately −900 to −400 mainly correspond to lung structures in the thoracic CT scan.

As mentioned above, other features such as the liver, kidney, bone or enhanced vessels may be chosen. The vessels are enhanced by injecting contrast media into the bloodstream. The image is thresholded to separate pixels corresponding to the liver or kidney, or to bone or enhanced vessel. Since these organs and features may be relatively small, it is preferable that higher resolution scanning is used with a thinner slice.

Figure 3:
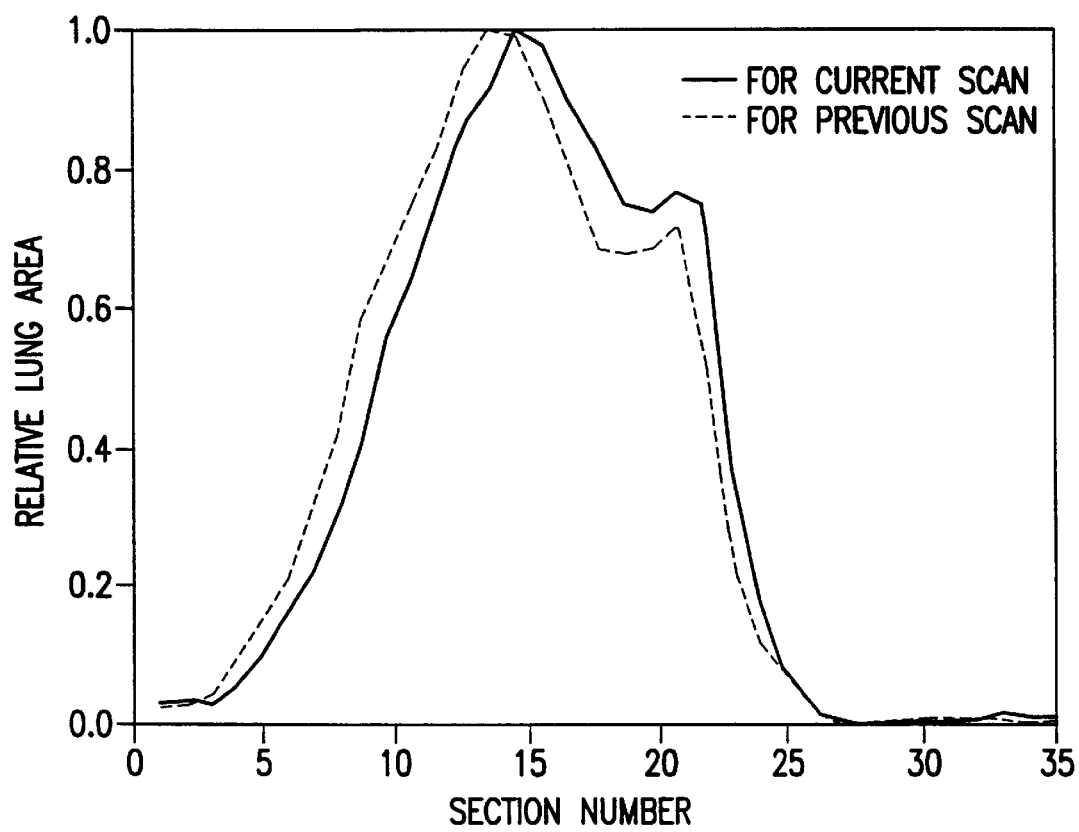
FIG. 3 is a graph of the relative lung area versus section number for the CT scans shown in FIGS. 2A and 2B.

FIG. 3 shows the relative lung area plotted for each section for the two CT scans in FIGS. 2A and 2B. Obviously, the value of the relative lung area was very small (close to zero) for sections in the abdomen and neck areas. Lung sections are selected from the scan that have a certain relative lung area. In this example, a lung section was selected from the scan if the relative lung area was larger than 0.1. Other ratios may be chosen.

Once the portions of the images that contain the anatomic feature are identified, the correspondence between the first and second images is determined (step 14). The selected lung section images from both the current and previous thoracic CT scans are used to determine the section correspondence between the two scans. First the curves of relative lung area (see FIG. 3) of the two scans are generated and compared to determine, approximately, the shift in the scanning direction (i.e., in the z-axis) between the two scans (step 15). The average section number of each curve was then calculated by summation of each weighted section number with its corresponding value of the relative lung area. The average section numbers are 14.7 and 13.7 for the curves of relative lung area of the current and previous scans in FIG. 3, respectively. The difference in the average section number between the two scans is related to the starting positions in the two consecutive scans. Therefore, the difference between the two average section numbers indicated the overall shifts in the scanning direction (i.e., in the z-axis) between the two scans. Intuitively, for the same patient, if the table position and the patient scanning starting position were kept the same in the two consecutive scans, then the two curves of the relative lung area should match exactly, and the two average section numbers should be the same. However, it is very difficult to keep these positions unchanged in a clinical environment.

In the two images a point is selected as an initial benchmark for finding the correspondence between the two images. For the thoracic CT scan example, the section image whose section number equals the nearest integer of its average section number is defined as the mid-section image of the scan. The mid-sections of the current and previous scans were used as the initial benchmark. The mid-section and several adjacent sections (two above and two below, a total of five sections, for example) are selected from the previous scan for comparison, one by one, with the mid-section from the current scan to find a pair of the best-matched section images in the two scans at the region around the mid-lung. For this comparison, the matching of the overall lung shape is more important than the detailed structures, such as vessels in the lungs.

A cross-correlation technique is used (step 15) to compare the mid-section image of the current scan to each of the selected (five) section images of the previous scan. To apply the cross-correlation technique, region-of-interest (ROI) images selected from the five section images of the previous scan are used instead of the section images themselves. Each ROI image has a width and height large enough to encompass the lungs for each section. In this example, the width and height of the ROI are 200 and 126 pixels, respectively. The center of the ROI for a section image is selected as the center of the lung area of that section image. FIG. 4A is an example of a section image while FIGS. 4B–4F are examples of the ROI section images selected for this comparison.

The normalized cross-correlation values between the mid-section of the current scan and each of the five ROIs of the previous scan were then calculated. The pair of sections which provided the highest cross-correlation value was identified as the corresponding section pair between the current and previous scans. The remaining sections in both scans were then correlated rigidly based on the determined corresponding pair with the highest cross-correlation value, i.e., in a one-to-one manner. Any remaining unpaired sections are ignored for further processing.

In a three-dimensional scan, such as a CT scan, a number of sections or slices are reconstructed. These slices are generally treated as having x-axis and y-axis data, while the scanning is preformed in the z-axis direction. Thus, the present invention matches corresponding sections or slices in the previous and current images two-dimensionally, in the x- and y-axis directions, and matches the scans (containing a number of section or slices) three-dimensionally in the z-axis direction.

Figure 5A:
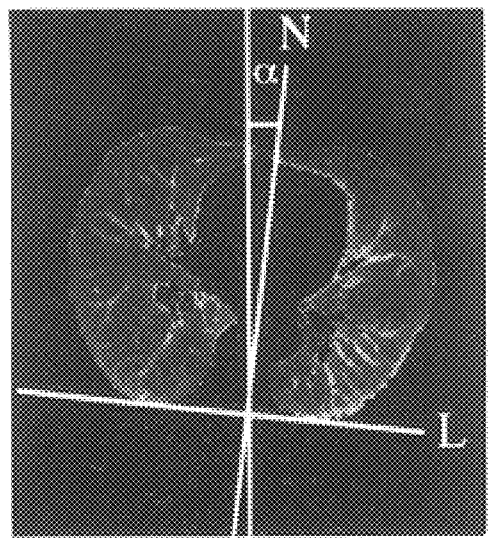
FIG. 5A is an image illustrating the definition of the orientation of the lungs.

After the establishment of the one-to-one section correspondence in the current and previous images, i.e. matching in the scanning direction (three-dimensional matching), the initial registration of the paired section images is performed in step 16 (two-dimensional matching). For the CT sections, each pair of corresponding section images in the two scans are initially registered. The initial registration of the corresponding section images in the two scans included two steps: a rotation correction and the determination of vertical and horizontal shifts of the previous section image relative to the current section image. The lungs in the thoracic CT section images were often oriented toward the right or left side because of patient movement, breathing, and lying on the back improperly during the scanning. FIG. 5A illustrates a section image with the lungs oriented to the left side. Commonly, the lung orientation is only slightly different for different sections in a given scan. However, the difference in lung orientations could be very large for sections from different scans.

Figure 5B:
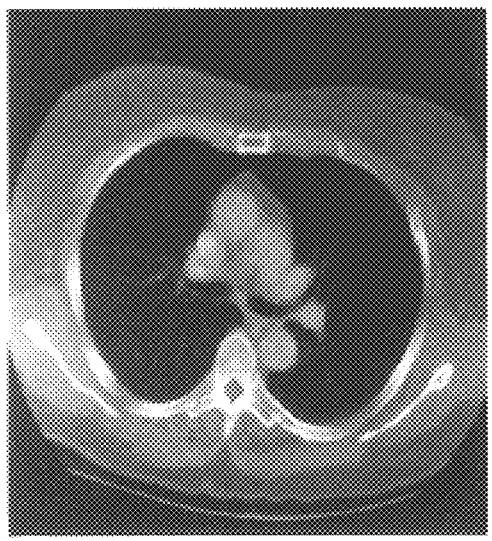
FIG. 5B is the image of FIG. 5A before rotation correction for lung orientation.
Figure 5C:
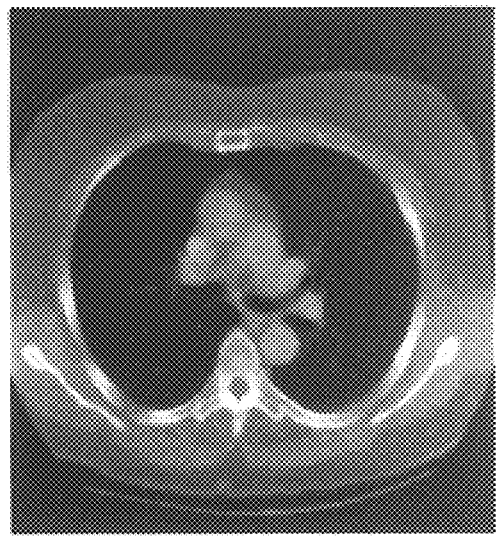
FIG. 5C is the image of FIG. 5A after rotation correction for lung orientation.

The lung orientation is defined by the angle ($\alpha$) between the vertical axis (Y axis) of the section image and the normal line (N) to the line segment (L) which goes through the lowest points in each lung, as illustrated in FIG. 5A. The orientation of each section image in both the current and previous scans was determined and corrected using known techniques. FIGS. 5B and 5C show an example of before and after the rotation correction for the orientation of the section image of FIG. 5A.

Figure 6A:
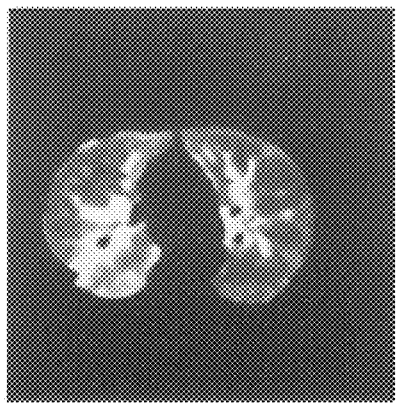
FIG. 6A is a section image from a current scan.
Figure 6B:
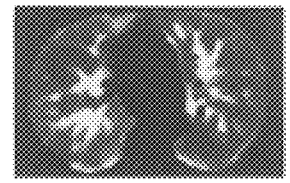
FIG. 6B is a corresponding ROI section image from a previous scan.
Figure 6C:
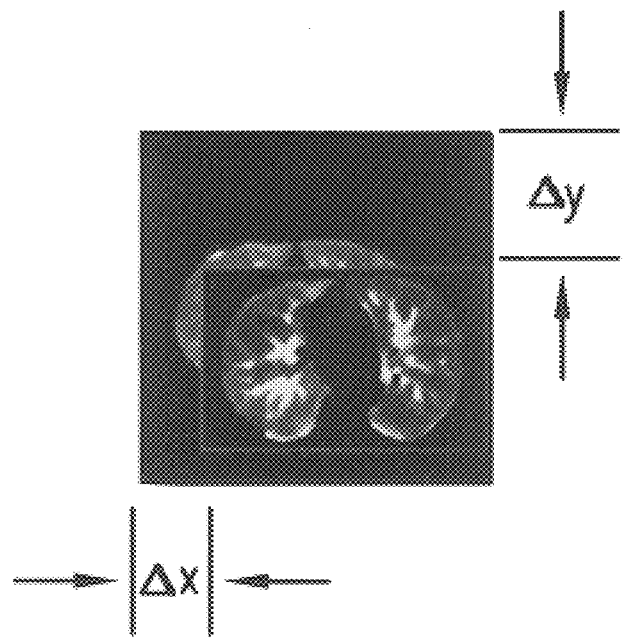
FIG. 6C is a diagram illustrating the definition of horizontal and vertical shifts ($\Delta x$ and $\Delta y$) of the image of FIG. 6B relative to the image of FIG. 6A.

The relative shifts in the vertical and horizontal directions between the previous section image and the corresponding current section image were determined also by use of the cross-correlation technique with the segmented, low-resolution images, as shown in FIG. 6. The similar ROI image (200×126 pixels, including the entire lungs) from the previous section image was again used for this purpose. The ROI image was moved through the current section image pixel by pixel, and the normalized cross-correlation value at each pixel was obtained. The horizontal and vertical shifts ($\Delta x$ and $\Delta y$) of the previous section image relative to the current section image were determined when the cross-correlation value reached its maximum value, as shown in FIG. 6B.

Figure 7A:
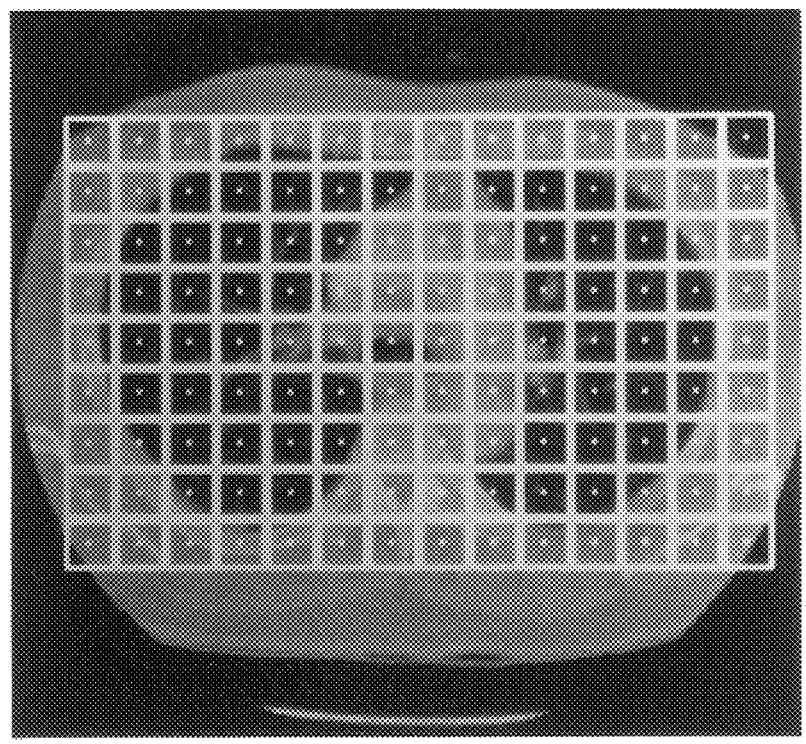
FIGS. 7A and 7B are diagrams illustrating the distribution of template ROIs on a previous section image and the distribution of search area ROIs on a current section image, respectively.
Figure 7B:
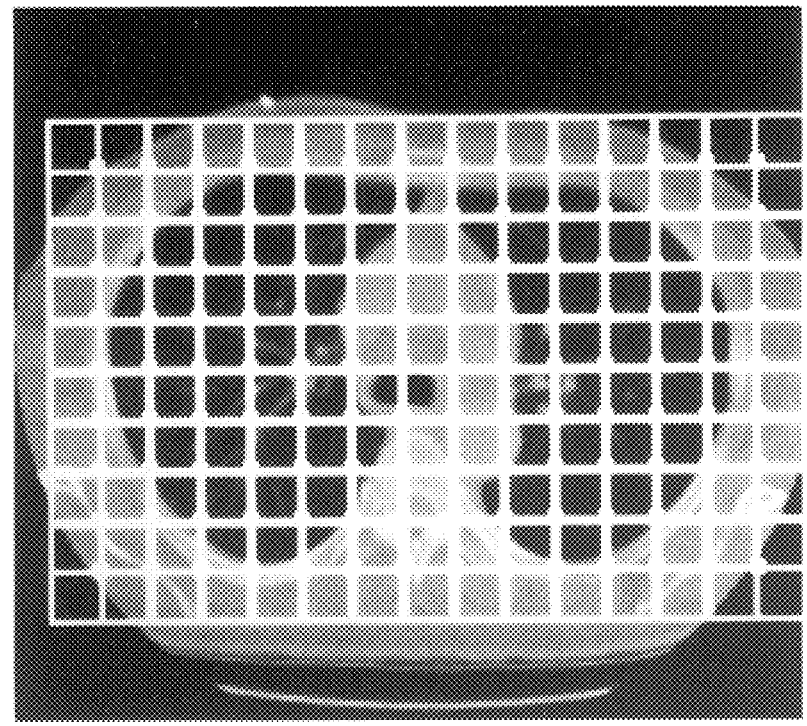

After the process of initial registration, local matching is applied to the images to obtain more accurate registration (step 17). For the CT scans, the corresponding pair of sections of the current and previous scans are locally matched. The local matching technique is again based on the cross-correlation technique, which results in nonlinear warping of the previous section image. To perform the local matching, many small ROIs were selected automatically over the lung area of the section image, as shown in FIGS. 7A and 7B. Recall that the lung area in the section image was approximated by a rectangle. An ROI selected in the previous section image is called a template ROI (or simply a template), and that selected in the current section image is called the search area ROI. The sizes of the template and search area ROIs were 16×16 and 32×32 pixels, respectively. Other sizes may be used. The distance between the centers of the two adjacent ROIs was fixed as 16 pixels for both the template and search area ROIs. For each pair of template and search area ROIs, the template was moved through the search area ROI pixel by pixel. The normalized cross-correlation value at each pixel was calculated. The maximum value of the cross-correlation indicated that the subregion in the search area ROI where the template overlapped was the "best" match with the template. The assignment of the template and search ROIs could be reversed, i.e., the search ROI could be selected in the previous section image.

Figure 8A:
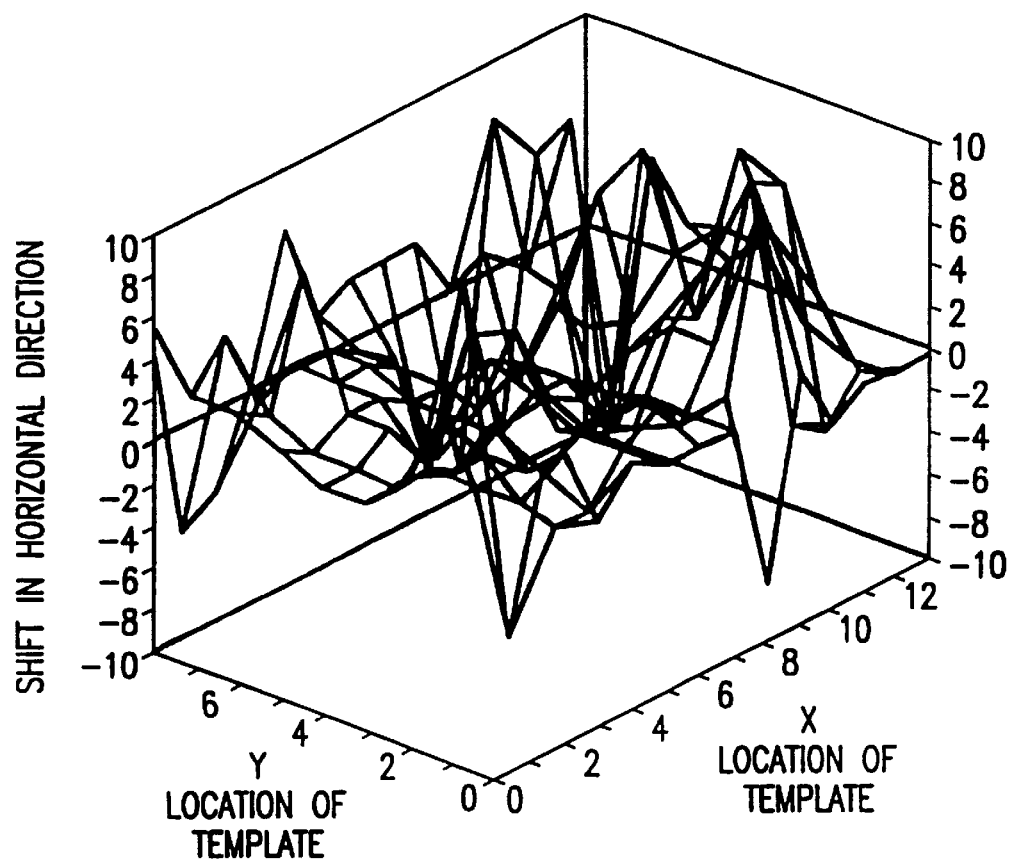
FIG. 8A is a diagram illustrating horizontal shifts ($\Delta x$) of all pairs of templates relative to the search area ROIs.
Figure 9A:
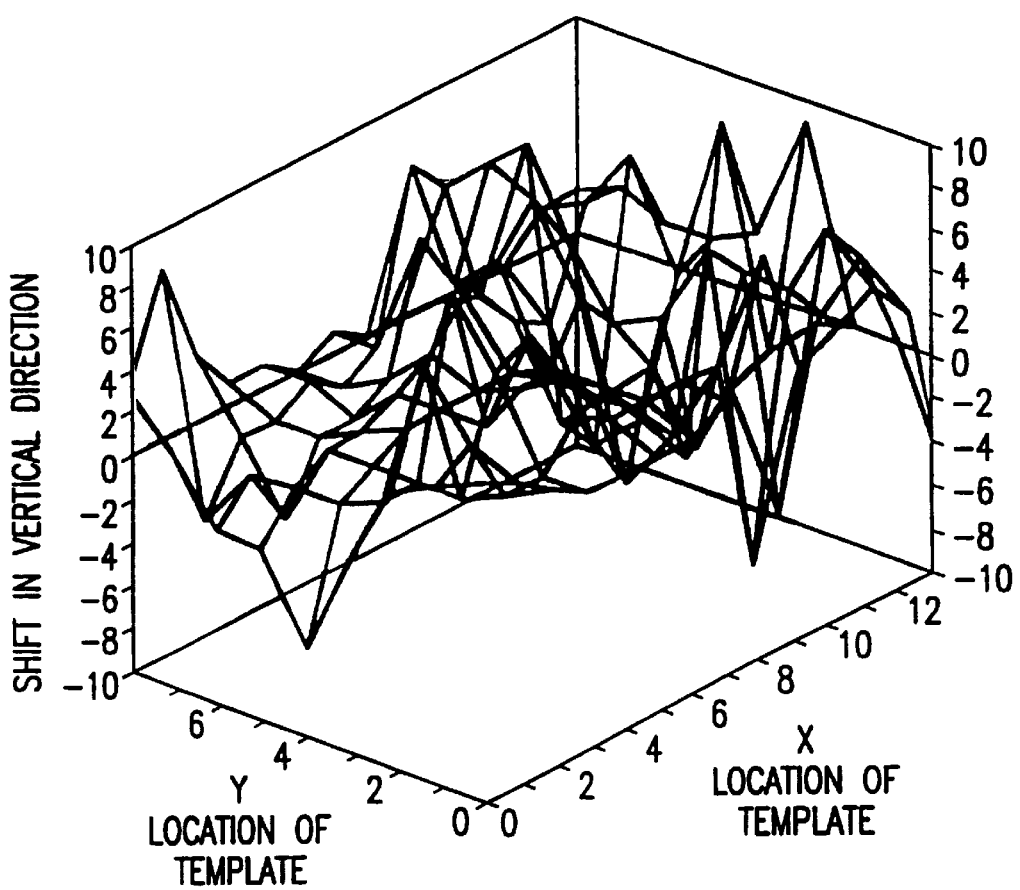
FIG. 9A is a diagram illustrating vertical shifts ($\Delta y$) of all pairs of templates relative to search area ROIs.

The horizontal and vertical shifts ($\Delta x$ and $\Delta y$) between the center of the template and the center of the search area ROI for the best match was thus determined. FIGS. 8A and 9A indicate the distributions of the shift values $\Delta x$ and $\Delta y$, respectively, derived for all pairs of template and search area ROIs in FIGS. 7A and 7B. It should be noted that the local matching should be limited to the area of the anatomic feature in the images (i.e., the lung area in the section images).

Figure 8B:
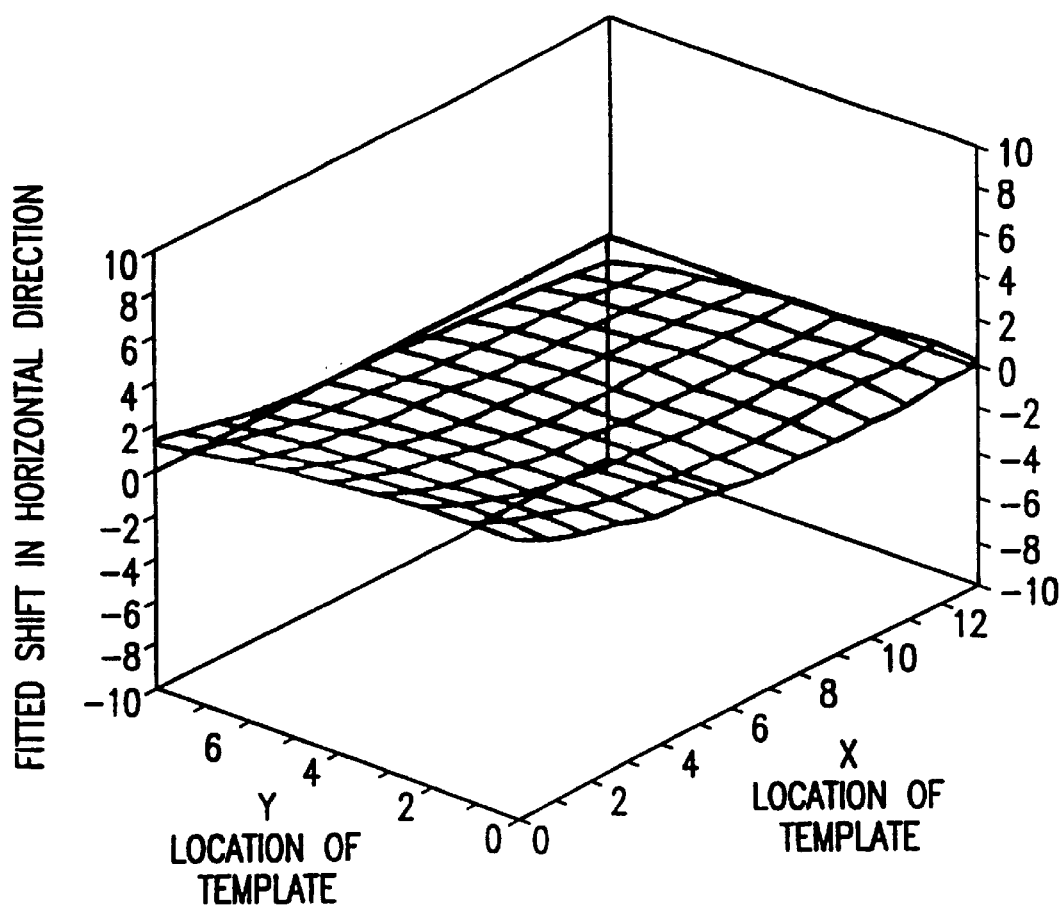
FIG. 8B is a diagram of a two-dimensional third-order polynomial fit of the horizontal shifts.
Figure 9B:
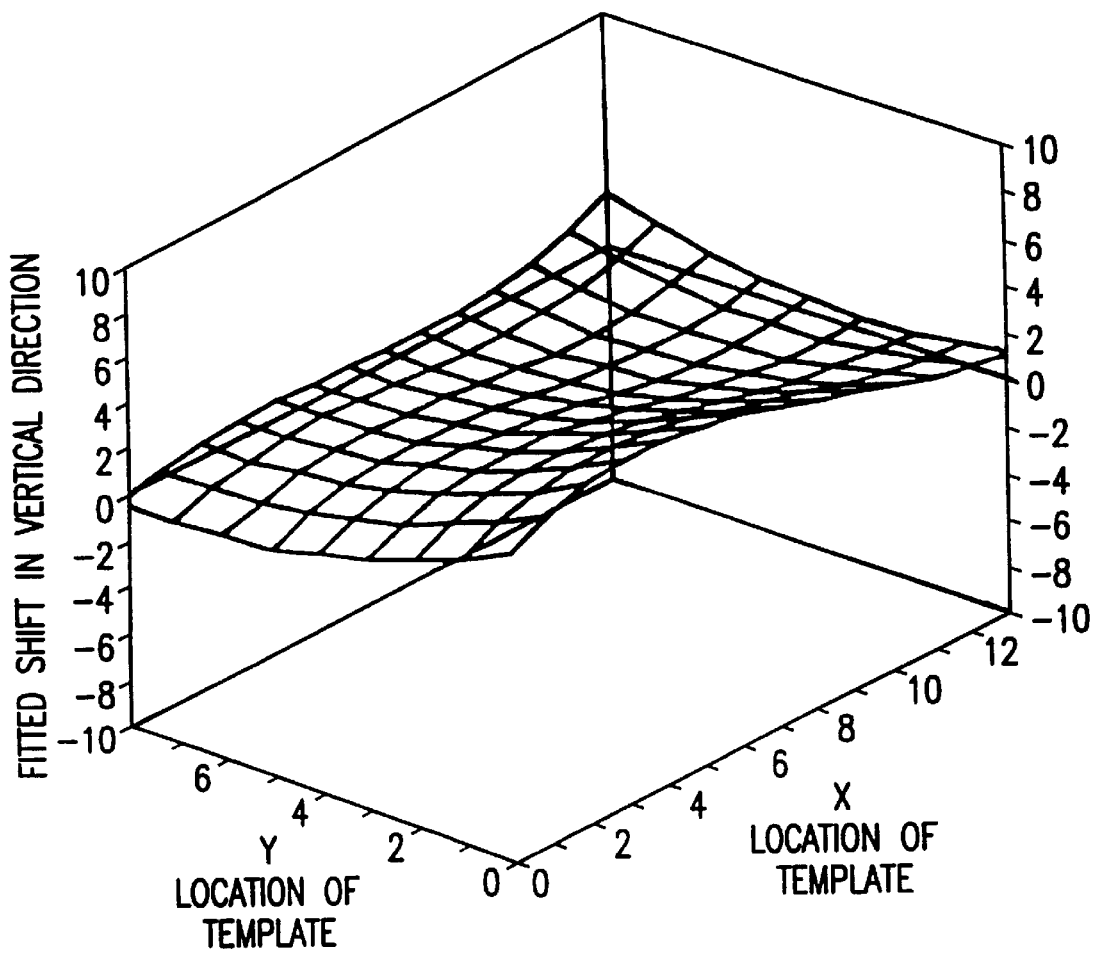
FIG. 9B is a diagram of a two-dimensional third-order polynomial fit of the vertical shifts.

A two-dimensional curve fitting with third-order polynomials, based on a least-squares method, was used for fitting $\Delta x$ and $\Delta y$ in order to obtain the continued shift values at each pixel for the purpose of nonlinear warping of the previous section image. Other curve fitting techniques may also be used. FIGS. 8B and 9B illustrate the fitted shift values of $\Delta x$ and $\Delta y$, respectively, at every pixel of the previous section image within the lung area, as shown in FIGS. 7A and 7B.

Figure 10A:
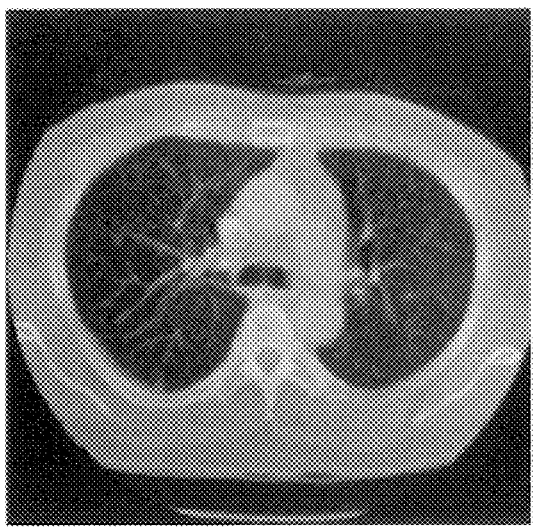
FIG. 10A is an original section image from a previous scan.
Figure 10B:
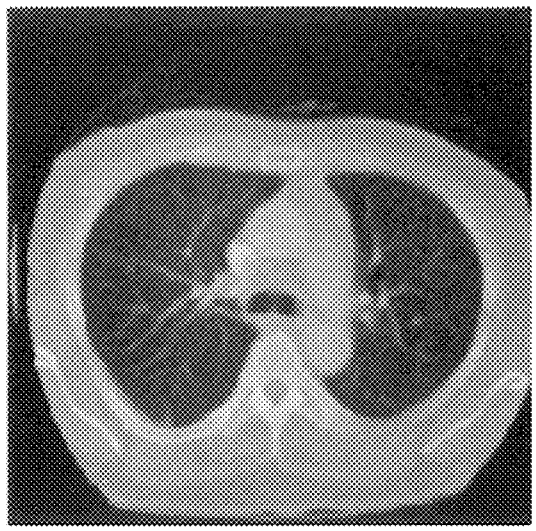
FIG. 10B is the section image of FIG. 10A after nonlinear warping.

To obtain the subtracted section image between the current and previous sections, the previous section image was warped (step 18) and then subtracted (step 19) from the current section image. The warping of the previous section image is based on the fitted shift values, as described in detail U.S. Pat. No. 5,319,549, application Ser. No. 08/900, 362, and Kano et al., Digital image subtraction of temporally sequential chest images for detection of interval change, Med Phys, vol. 2, No. 1 pp. 453–461 (1994). FIGS. 10A and 10B illustrate a previous section image and its warped image.

EXAMPLE

A total of 14 cases (14 pairs of temporally sequential thoracic CT scans) were used to demonstrated the method according to the invention. The time interval between the current and previous thoracic CT scans was varied from two to seven months. The truth of the presence or absence of interval changes was obtained by an experienced radiologist reading the images. Two cases were reported to have interval changes, and the other cases had no interval changes, according to the radiologists.

Figure 11A:
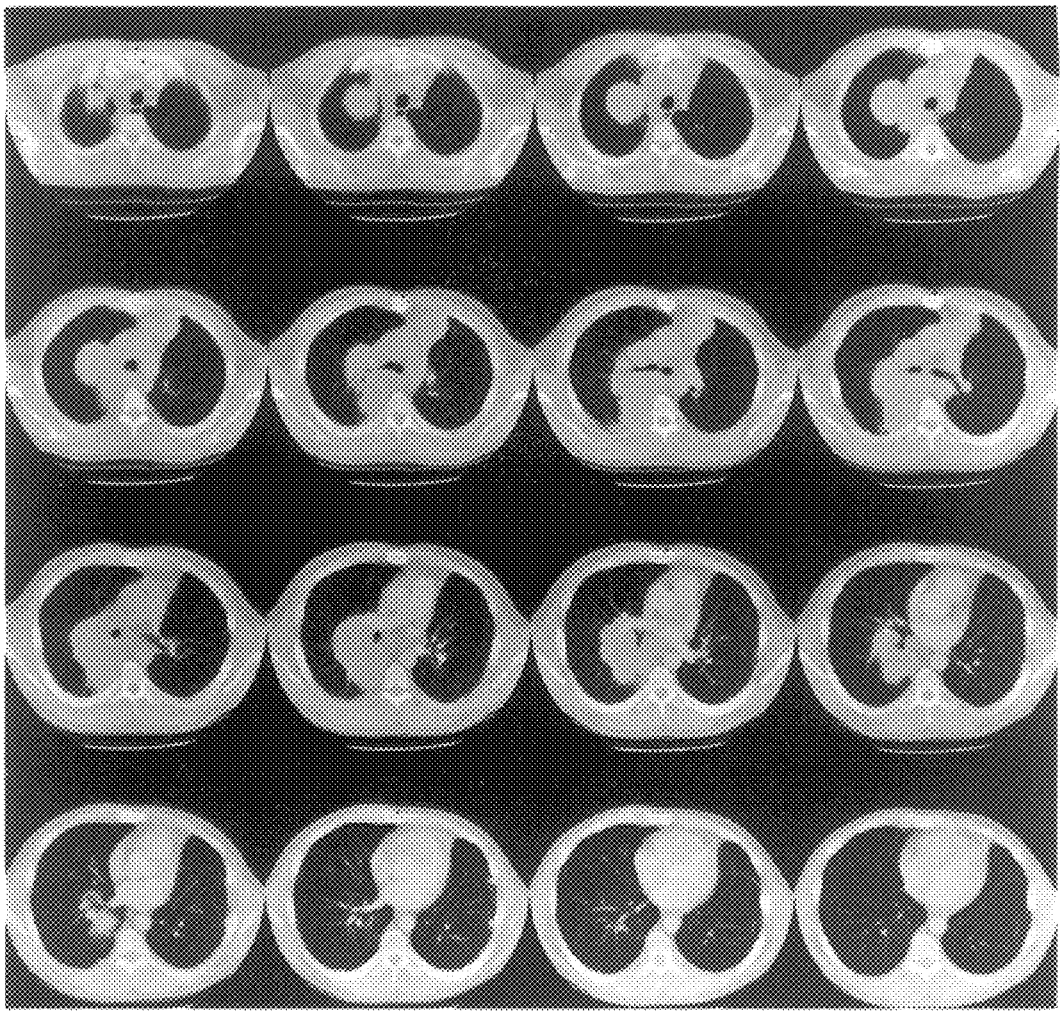
FIG. 11A is a diagram of section images of a current scan.
Figure 11B:
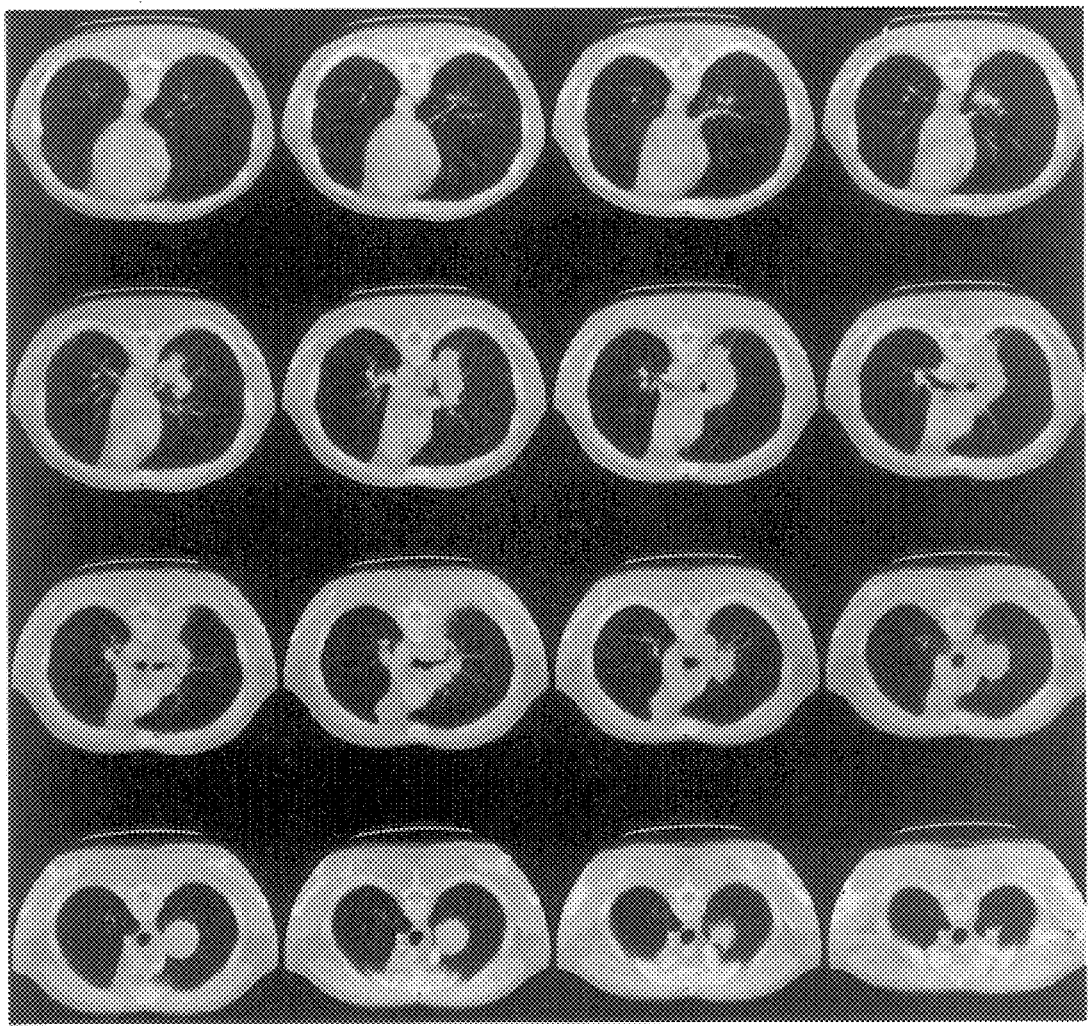
FIG. 11B is a diagram of section images of a previous scan.
Figure 11C:
FIG. 11C is a diagram of the subtracted section images obtained using the images of FIGS. 11A and 11B.

FIGS. 11A–11C show the case in which an anterior mediastinal mass (at the left side in the section images) increased in size from 3 cm in the previous scan to 4 cm in the current scan. On the subtracted section images (FIG. 11C), the dark area surrounding the mass indicates that the mass is increased in size. The dark area is indicated by the arrows. With the method according to the invention, the new findings or interval changes in the current sections are shown as dark patterns on the subtracted section images. Also, for this case, the right hilar region had increased in size in the current section images; this was again shown as a dark region in the subtracted section images, as also seen in FIG. 11C.

Figure 12A:
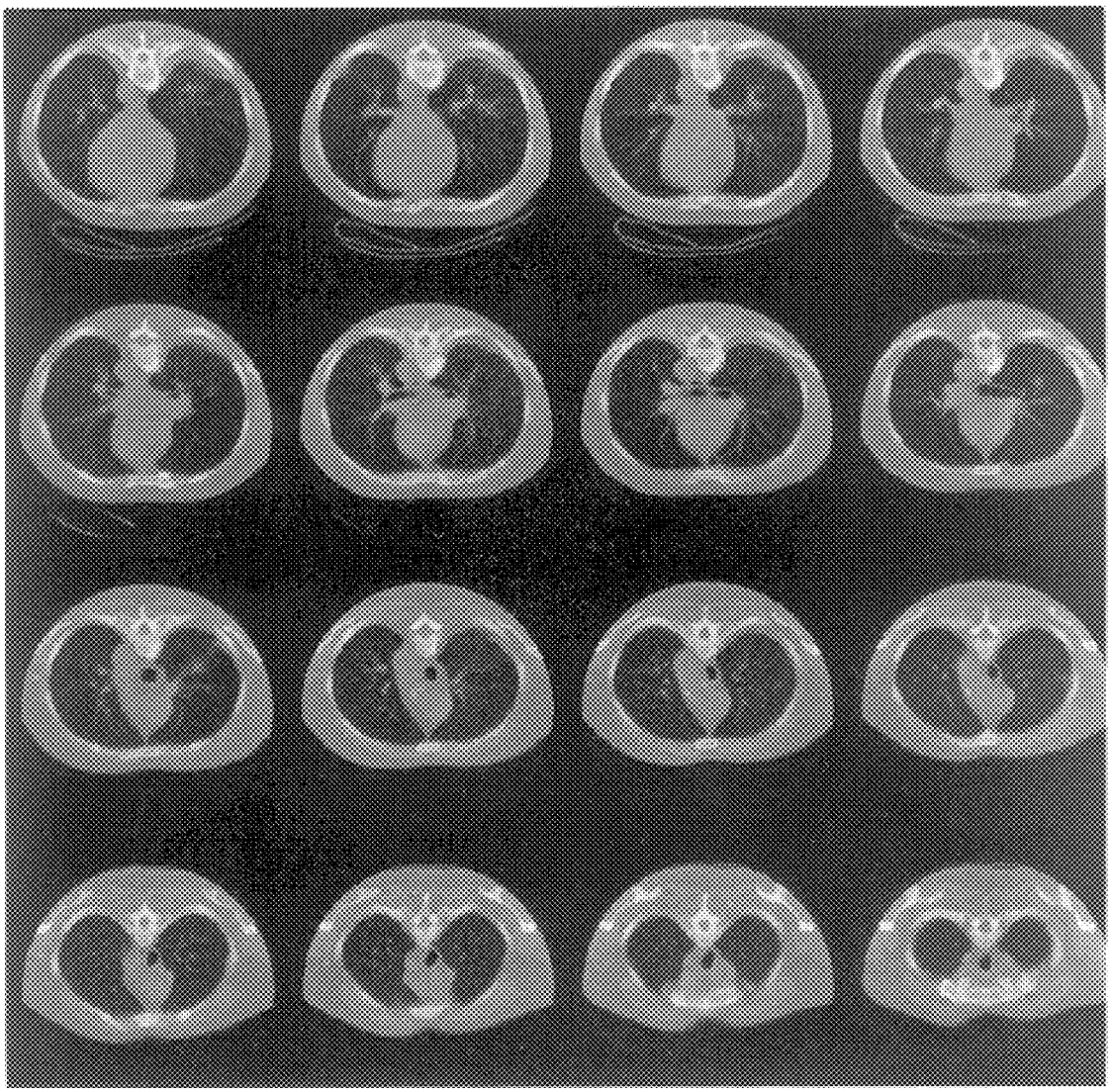
FIG. 12A is a diagram of section images of a current scan.
Figure 12B:
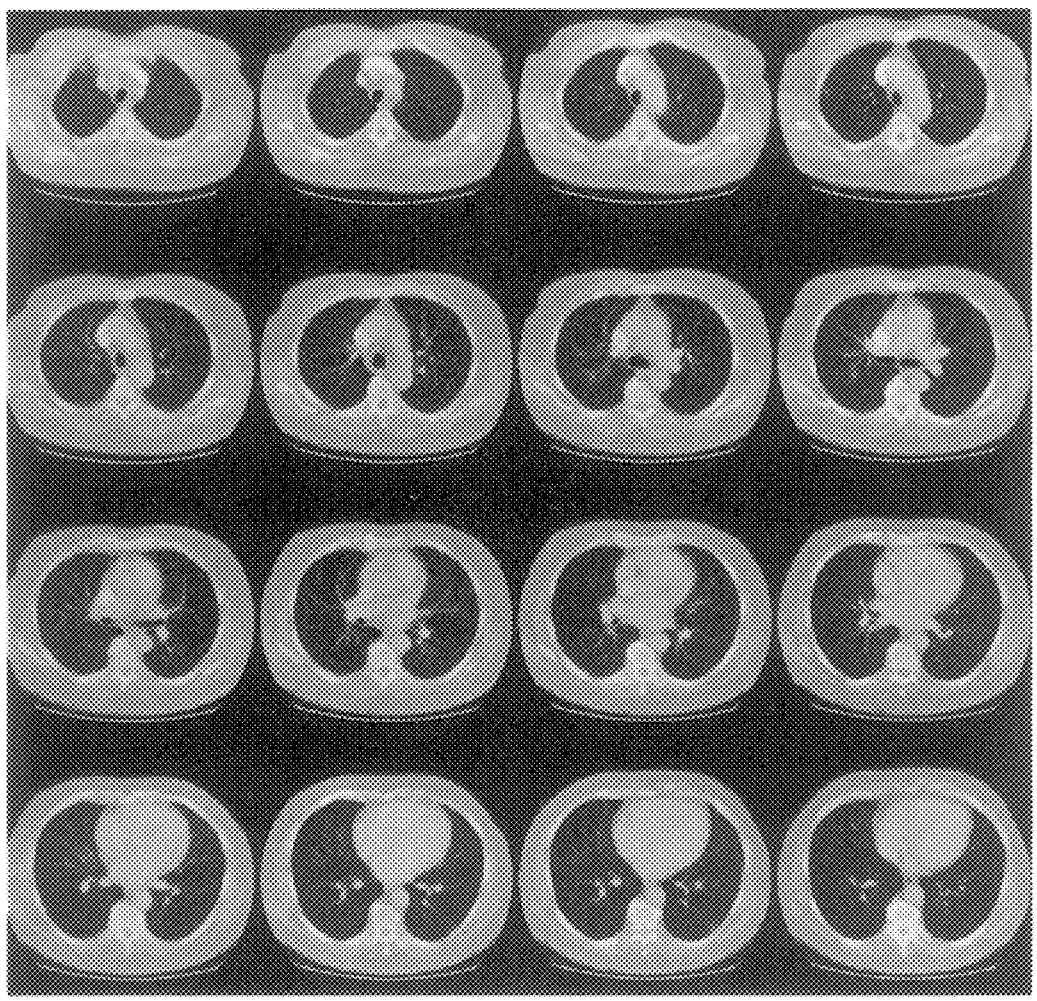
FIG. 12B is a diagram of section images of a previous scan.
Figure 12C:
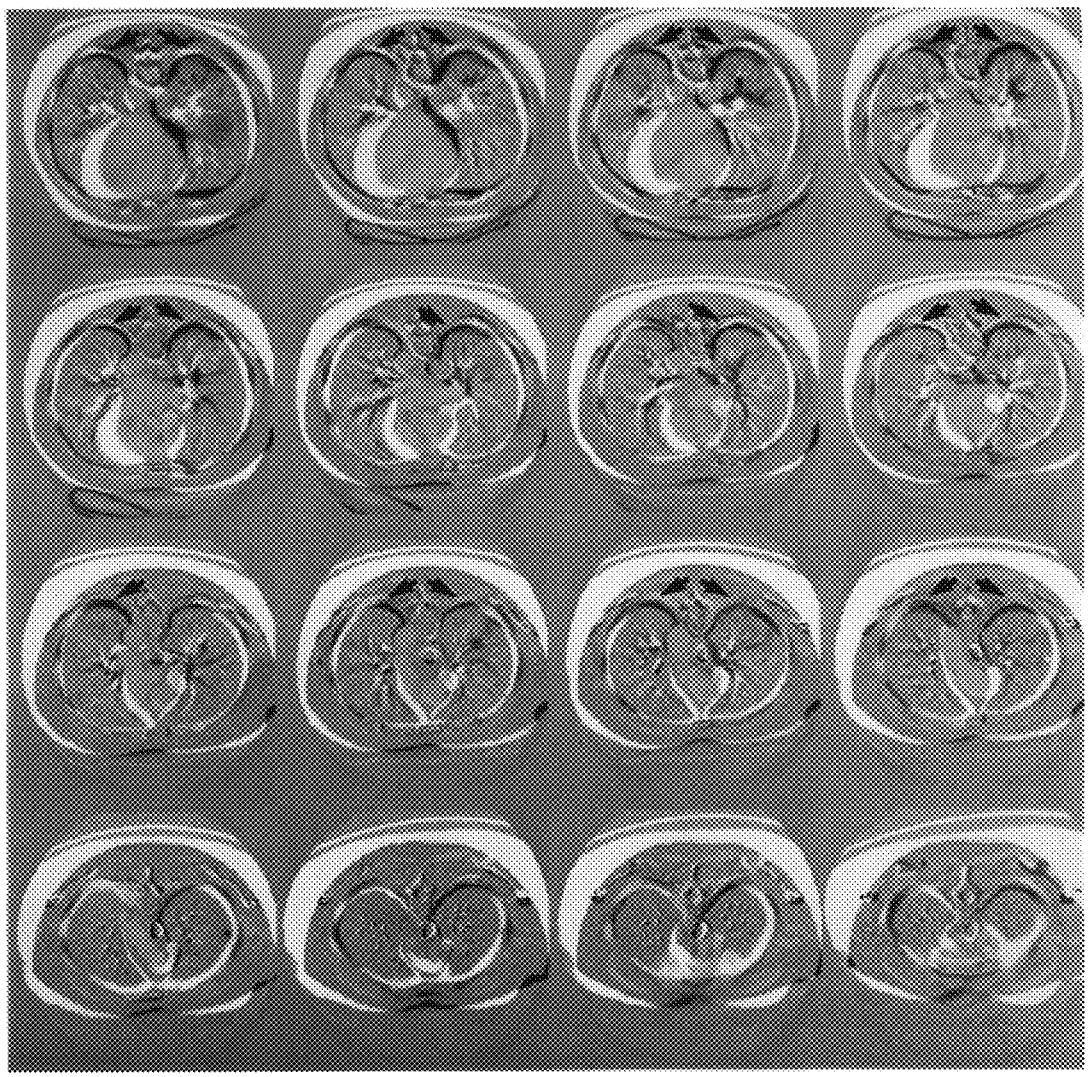
FIG. 12C is a diagram of the subtracted section images obtained using the images of FIGS. 12A and 12B.

FIGS. 12A–12C show another case of temporal subtraction, in which a new pleural effusion (indicated by the arrows in FIG. 12C) developed at the lung bases in the current section images. The newly developed pleural effusion may be due to metastatic disease or to another cause. On the subtracted section images (FIG. 12C), the dark structures with a waning moon shape in the left and right lower parts of the lungs illustrate the newly developed symptom.

It will be noted that some vascular structures remained in the subtracted section images. The main reason for misregistration of these vascular structures in the current and previous sections was probably the partial volume effect due to the variation in the depth of patient inspiration during the scan, and also to the different starting positions for the scans in the two sequential CT examinations. Although it is difficult to control patient breathing in different scans, it is possible to overcome the partial volume effect caused by the different starting positions in two sequential scans, if the raw data from the helical scanning are available.

In a modification of the method according to the invention, the raw scanning data are obtained (step 19) and the section images of a helical scan can be reconstructed for different starting locations on the z-axis from the data (step 20). In the clinical situation, the reconstruction usually starts at the position where the scanning starts physically. The registration of the corresponding sections in two scans can be greatly improved if the reconstruction starting position of one scan can be properly adjusted within the range of one section thickness (i.e., 10 mm in this example), with an accuracy on the order of 1 mm. Whether to use the raw data to reconstruct the images may be determined using histogram analysis and subtracted image to determine the degree of misregistration. The histogram has a broader distribution when there is misregistration since there are more light and dark patterns in the subtracted image. On the other hand, the histogram has a narrower distribution when there are fewer light and dark patterns. A measure of the breadth or narrowness of the histogram may be used to automatically determine if the registration is acceptable.

If the histogram analysis shows that there is significant misregistration, the current image may be reconstructed using a different starting point. The new starting point can be determined iteratively by shifting the previous starting point by a fixed distance, such as 1 mm. The scanner has the capability of image reconstructing based on a number of input parameters, including starting a reconstruction at any point with a section. The input parameters may be adjusted to produce a better match of the current and previous images. The method according to the invention is repeated with the newly reconstructed images. When the registration is found to be acceptable using the histogram analysis, the images can be output.

Figure 13:
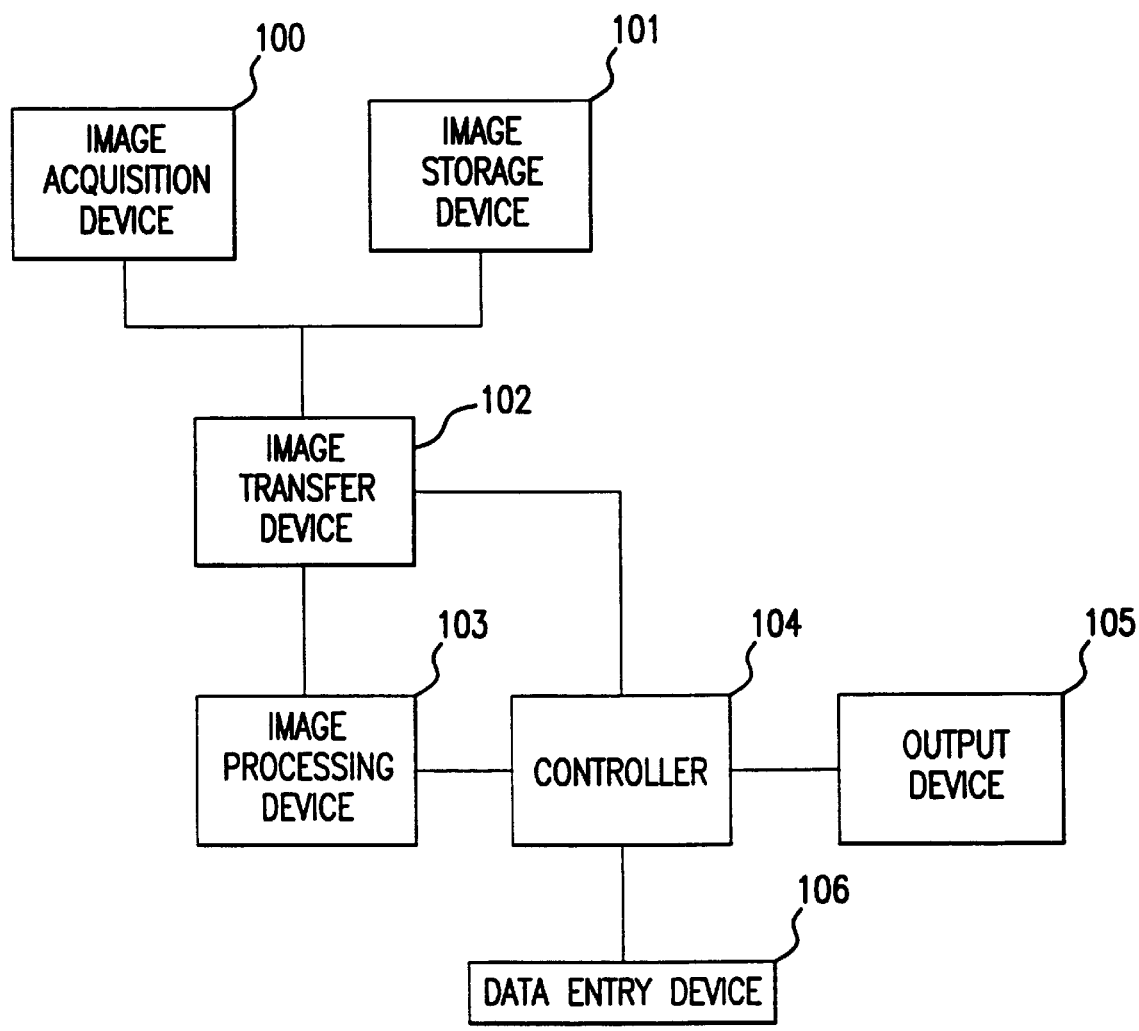
FIG. 13 is a diagram of the system according to the invention.

FIG. 13 is a diagram of the system according to the invention. Images (or data) is obtained from image acquisition device 100 and image storage device 101. Image acquisition device 100 may be a CT scanner or an MRI scanner, for example. Image storage device 101 may be a memory device, an optical disk reader, when the images or data are stored on optical disk, or the PACS system (picture archiving communication system) where the images are usually stored on magnetic tape. An image transfer device 102 transfers images from devices 100 and 101 to image processing device 103. Device 103 carries out the operations described above in connection with the method embodiment. For example, device 103 processes the image by conducting the thresholding operation on the images and the Gaussian filtering. Device 103 also performs the relative area determinations, matching and cross-correlations, as well as the warping and subtracting. Device 103 may contain memory to store data or images on which the operations are being carried out, or intermediate results.

Devices 100–103 are controlled by a controller 104. Controller 104 may be, for example, a computer. Controller 104 also controls the output or display of the results of device 103 sent to output device 105. Output device 105 may be a video display terminal or a printer. A data entry device 106, such as a keyboard and pointing device, is provided to enter commands for the controller 104 to control the various devices to carry out the operations on the images or image data.

The system according to the invention may also be implemented in software run on a computer. Software code devices maybe written to carry out the various operations on the images. Thus, the invention may also be implemented as a program embedded in a computer-readable storage medium, such as a magnetic or optical disk.

Figure 14:
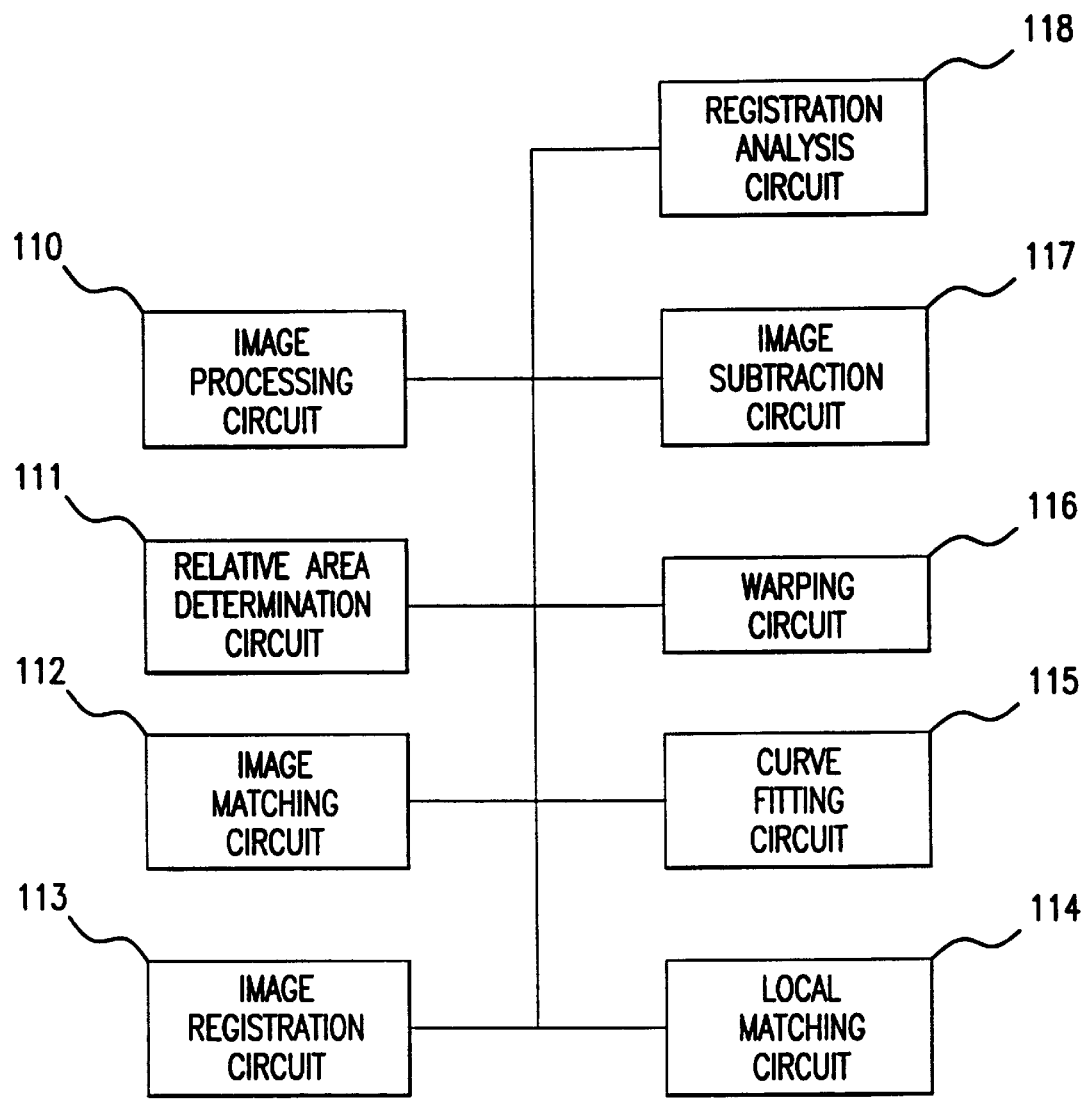
FIG. 14 is a diagram of the image processing device according to the invention.

FIG. 14 is a more detailed diagram of device 103. Device 103 includes an image processing circuit 110 that performs thresholding and, if needed, filtering operations or other desired image processing. The image after processing by circuit 110 used by circuit 111 to determine the relative area of an anatomic feature, such as the lungs. Image matching circuit 112 performs the cross-correlation to determine the initial registration of the two images, and ROI selection in the images for this operation. In the CT example, the mid-section image from the current is compared with the five selected section images from the previous scan using the cross-correlation operation to match the two scans.

Image registration circuit 113 performs the rotation correction and the determination of the vertical and horizontal shifts, using the matched images.

Local matching circuit 114 locally matches the images (the section pairs in the CT example) for accurate registration. Template and search ROIs are selected and the distribution of the horizontal and vertical shifts are determined using cross-correlation.

A curve-fitting circuit 115 fits the distribution of the horizontal and vertical shifts using a polynomial fit, as discussed above. The fitted distribution is used by warping circuit 116 to produce the warped image, which is subtracted by subtraction circuit 117 from the current image to produce the subtracted images.

The circuit may also contain a registration analysis circuit 118 that determines if the registration is acceptable. If the registration is not found to be acceptable, using histogram analysis, for example, the circuit causes the system to obtain the image data (CT scanning data in this example) and the data is used by the image acquisition device to reconstruct the section images at a more desired starting point to eliminate image artifacts such as the partial volume artifact. This operation may be done iteratively.

The automated registration and subtraction method and system according to the invention, particularly when applied to temporally sequential section images, can enhance some interval changes effectively, such as changes in tumor size and the development of new nodules and pleural effusions. Therefore, the method and system according to the invention may help radiologists to identify and assess subtle interval changes in thoracic CT examinations more quickly and accurately.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for detecting interval change, comprising:
   obtaining a first three-dimensional image of a subject by scanning said subject in a scanning direction;
   obtaining a second three-dimensional image of said subject by scanning said subject in said scanning direction;
   matching three dimensionally said first and second images in said scanning direction;
   matching two-dimensionally said first and second images after matching in said scanning direction; and
   non-linearly warping said first image to produce a warped image after said three- and two-dimensional matching; and
   subtracting said warped image from said second image;
   wherein matching two-dimensionally comprises:
      selecting a first section of said first image based upon a feature in said first image;
      selecting a second section of said second image based upon said feature in said second image;
      selecting a plurality of sections adjacent to first section of said first image; and
      comparing each of said first section and said plurality of sections to said second section.

2. A method as recited in claim 1, comprising:
   determining a first relative area of said anatomic feature in said first image;
   determining a second relative area of said anatomic feature in said second image;
   selecting said first section using said first relative area; and
   selecting said second section using said second relative area.

3. A method as recited in claim 2, wherein determining said first and second relative area comprises:
   obtaining said first and second images each having a plurality of sections;
   thresholding sections said first image to obtain corresponding first regions;
   thresholding sections said second image to obtain corresponding second regions;
   determining an area of each of said first and second regions;
   determining first relative areas as a ratio of said areas of said first regions to remaining areas of corresponding sections of said first image; and
   determining second relative areas as a ratio of said areas of said second regions to remaining areas of corresponding sections of said second images.

4. A method as recited in claim 3, wherein said matching comprises:
   comparing said first and second relative areas.

5. A method as recited in claim 1, wherein said matching two-dimensionally comprises:
   obtaining said first and second image each having a plurality of sections;
   determining a first relationship of an area of an anatomic feature in respective sections in said first image;
   determining a second relationship of an area of said anatomic feature in respective sections in said second image;
   determining a first average and a second average of said first and second relationships, respectively;
   selecting said first section of said first image corresponding to said first average; and
   selecting said second section of said second image corresponding to said second average.

6. A method as recited in claim 1, comprising:
   selecting a region-of-interest in said first section and each section of said plurality of sections; and
   cross-correlating said regions-of-interest with said section of said second image.

7. A method as recited in claim 1, wherein said comparing comprises:
   cross-correlating said first section and each of said plurality of sections with said one section of said second image.

8. A method as recited in claim 1, comprising:
   matching a section from said plurality of sections with said second section of said second image; and
   matching remaining sections of said first image with remaining sections of said second image.

9. A method as recited in claim 1, comprising:
   obtaining each of said first and second images as digital images each having a plurality of pixels;
   thresholding each of said first and second images to identify feature pixels corresponding to an anatomic feature;
   determining a first relative area of said anatomic feature as a ratio of an area of feature pixels in said first image to an area remaining pixels in said first image;
   determining a second relative area of said anatomic feature as a ratio of an area of feature pixels in said second image to an area of remaining pixels in second image; and
   comparing said first and second relative areas to match said first image to said second image.

10. A method as recited in claim 9, wherein said comparing comprises:
   determining a first average value of said first relative area;
   determining a first section of said first image corresponding to said first average value;
   determining a second average value of said second relative area;

determining a second section of said second image corresponding to said second relative area; and comparing said first and second sections.

11. A method as recited in claim 1, wherein said matching comprises:

initially matching said first image to said second image; and locally matching said first image to said second image.

12. A method as recited in claim 11, wherein said initially matching comprises:

determining whether at least one of said first and second images are rotated and whether a rotation correction is required; and determining vertical and horizontal shifts of said first image relative to said second image.

13. A method as recited in claim 12, comprising:

using said vertical and horizontal shifts to match a section of said first image with a section of said second image; and matching remaining sections of said first image with remaining sections of said second image in a one-to-one manner.

14. A method as recited in claim 11, wherein said locally matching comprises:

selecting a plurality of first ROIs in said first image;

selecting a plurality of second ROIs in said second image; and determining horizontal and vertical shifts of said first ROIs in said first image relative to said second ROIs in said second image.

15. A method as recited in claim 14, comprising:

curve-fitting said horizontal and vertical shifts; and nonlinearly warping said first image using curve-fit horizontal and vertical shifts.

16. A method as recited in claim 1, comprising:

obtaining a first CT scan as said first three-dimensional image;

obtaining a second CT scan as said second three-dimensional image;

selecting a first set of sections from said first CT scan using an anatomic feature in said first CT scan; and selecting a second set of sections from said second CT scan using said anatomic feature in said second CT scan.

17. A method as recited in claim 16, comprising:

obtaining a first CT scan as said first CT scan;

obtaining a second thoracic CT scan as said second CT scan;

selecting said first set from said first CT scan using a lung in said first CT scan; and selecting said second set from said second CT scan using said lung in said second CT scan.

18. A method as recited in claim 17, comprising:

determining a first relative area of said lung in said first CT scan;

determining a second relative area of said lung in said second CT scan;

selecting said first set using said first relative area; and selecting said second set using said second relative area.

19. A method as recited in claim 18, wherein determining said first and second relative area comprises:

thresholding said first CT scan to obtain first regions corresponding to said lung;

thresholding said second CT scan to obtain second regions corresponding to said lung;

determining an area of each of said first and second regions;

determining first relative areas as a ratio of said areas of said first regions to remaining areas of corresponding sections in said first set; and determining second relative areas as a ratio of said areas of said second regions to remaining areas of corresponding sections in said second set.

20. A method as recited in claim 19, comprising:

selecting said first section of said first CT scan using said first relative areas;

selecting said second section of said second CT scan using said second relative areas; and registering said first section and said second section.

21. A method as recited in claim 20, comprising:

matching one of said first section and said sections adjacent to said first section to said second section.

22. A method as recited in claim 21, comprising:

matching remaining sections of said first CT scan with remaining sections of said second CT scan.

23. A method as recited in claim 1, wherein said matching two-dimensionally comprises:

determining a first area of an anatomic feature in said first image;

determining a second area of said anatomic feature in said second image;

comparing said first and second areas; and matching said first and second images based upon comparing said areas.

24. A method as recited in claim 23, comprising:

selecting said first section of said first image using said first area;

selecting said second section of said second image using said second area; and matching said first and second images based upon comparing said first and second sections.

25. A method as recited in claim 24, comprising:

matching said first and second images based upon comparing said first section and said plurality of sections with said second section.

26. A method as recited in claim 1, comprising:

identifying an anatomic feature in each of said first and second images;

identifying respective first and second approximate middle positions of said anatomic feature in said first and second images; and matching said first and second scans using said first and second approximate middle positions.

27. A method as recited in claim 26, comprising:

selecting a first section of said first image as corresponding to said first approximate middle position;

selecting said second section of said second image corresponding to said second approximate middle position; and matching two-dimensionally said first and second scans using said first and second sections.

28. A method as recited in claim 27, comprising:

matching two-dimensionally said first and second images based upon comparing said first section and said plurality of adjacent sections with said second section.

29. A method as recited in claim 1, comprising:

analyzing registration of said warped image and said second image;
if said registration does not meet predetermined criteria, retrieving image data corresponding to said first image and reconstructing said first image.

30. A method as recited in claim 29, wherein analyzing said registration comprises using histogram analysis.

31. A method as recited in claim 29, comprising:
reconstructing said first image at a different reconstruction starting point;
repeating said matching, warping and subtracting steps using said first image reconstructed at said different reconstruction starting point; and
re-analyzing said registration.

32. A method as recited in claim 31, comprising:
iteratively selecting said different reconstruction starting point.

33. A method for detecting interval change, comprising:
obtaining a first image of a subject;
obtaining a second image of said subject;
matching said first and second images three-dimensionally in a scanning direction using an anatomic feature in said first and second images;
matching said first and second images two-dimensionally after said three-dimensional matching; and
detecting an interval change after matching said first and second images three- and two-dimensionally;
wherein matching two-dimensionally comprises:
    selecting a first section of said first image based upon a feature in said first image;
    selecting a second section of said second image based upon said feature in said second image;
    selecting a plurality of sections adjacent to first section of said first image; and
    comparing each of said first section and said plurality of sections to said second section.

34. A method as recited in claim 33, where detecting comprises:
nonlinearly warping said first image; and
subtracting a warped first image from said second image.

35. A method as recited in claim 33, comprising:
obtaining a first three-dimensional image as said first image; and
obtaining a second three-dimensional image as said second image.

36. A method as recited in claim 35, comprising:
obtaining a plurality of first section images as said first three-dimensional image;
obtaining a plurality of second section images as said second three-dimensional image; and
matching said first and second section images along said scanning direction.

37. A method of detecting interval change, comprising:
obtaining a first scan of a subject having a plurality of sections;
obtaining a second scan of said subject having a plurality of sections;
matching three-dimensionally said first and second scans;
matching two-dimensionally corresponding sections of said first and second scans after matching three-dimensionally; and
detecting an interval change between said first and second scans after said matching steps;
wherein matching two-dimensionally comprises:
    selecting a first section of said first scan based upon a feature in said first scan;
    selecting a second section of said second scan based upon said feature in said second scan;
    selecting a plurality of sections adjacent to first section of said first scan; and
    comparing each of said first section and said plurality of sections to said second section.

38. A method as recited in claim 37, wherein matching three-dimensionally comprises matching said first and second scans in a scanning direction.

39. A method as recited in claim 37, comprising:
matching two-dimensionally said corresponding sections of said first and second scans in first and second directions orthogonal to each other; and
matching three-dimensionally said first and second scans in a third direction orthogonal to each of said first and second directions.

40. A method as recited in claim 39, wherein matching three-dimensionally comprises matching said first and second scans in a scanning direction.

41. A method as recited in claim 37, wherein matching three-dimensionally comprises:
identifying an anatomic feature in said first scan;
identifying said anatomic feature in said second scan; and
matching said first and second scans using said anatomic feature.

42. A method as recited in claim 41, comprising:
using said anatomic feature to select said first section of said first scan;
using said anatomic feature to select said second section of said second scan; and
matching said first scan with said second scan based upon said comparing step.

43. A method as recited in claim 42, comprising:
matching one of said first section and said plurality of adjacent sections with said second section; and
matching remaining sections of said first scan with remaining sections of said second scan.

44. A computer program product, comprising:
a computer storage medium and a computer program code mechanism embedded in the computer storage medium for processing an image generated in an image processing apparatus, the computer program code mechanism comprising:
    a first code device configured to match first and second images of a subject three-dimensionally in a scanning direction using an anatomic feature in said first and second images and two-dimensionally after said three-dimension matching;
    a second code device configured to detect an interval change in matched first and second images after said three- and two-dimensional matching;
    wherein said first code device is configured to:
        select a first section of said first image based upon a feature in said first image;
        select a second section of said second image based upon said feature in said second image;
        select a plurality of sections adjacent to first section of said first image; and
        compare each of said first section and said plurality of sections to said second section.

45. A computer program product as recited in claim 44, comprising:

said first code device configured to match three-dimensionally corresponding sections of said first and second images.

46. A computer program product as recited in claim 44, comprising:

a third code device configured to identify an anatomic feature in said first image; and said second code device configured to identify said anatomic feature in said second.

47. A computer program product as recited in claim 46, comprising:

a fifth code device configured to determine a first relative area of said anatomic feature in said first image;

a sixth code device configured to determine a second relative area of said anatomic feature in said second image;

a seventh code device configured to select a first set of said first image using said first relative area; and an eighth code device configured to select a second set of said second image using said second relative area.

48. A computer program product as recited in claim 47, comprising:

a ninth code device configured to determine a first average and a second average of said first and second relative areas, respectively;

said first code device configured to select one section of said first image corresponding to said first average; and said first code device configured to select one section of said second image corresponding to said second average.

49. A computer program product as recited in claim 46, comprising:

said first code device configured to use said anatomic feature to select a first section of said first image;

said first code device configured to use said anatomic feature to select a second section of said second image; and said first code device configured to match said first image with said second image based upon said comparing step.

50. A computer program product as recited in claim 49, comprising:

said first code device configured to match said first image with said second image based upon comparing said first section and said plurality of sections with said second section.

51. A computer program product as recited in claim 50, comprising:

said first code device configured to match one of said first section and said plurality of adjacent sections with said second section; and said first code device configured to match remaining sections of said first image with remaining sections of said second image.

52. A computer program product as recited in claim 44, comprising:

a third code device configured to nonlinearly warp said first image; and a fourth code device configured to subtract a warped first image from said second image.

53. An interval change detecting system, comprising:

one of a three-dimensional image acquisition device and a three-dimensional image storage device;

a scanning direction image matching device connected to one of said image acquisition device and said image storage device;

a two-dimensional image matching device connected to one of said image acquisition device and said image storage device, and adapted to:

select a first section of a first three-dimensional image based upon a feature in said first image;

select a second section of a second three-dimensional image based upon said feature in said second image;

select a plurality of sections adjacent to first section of said first image; and compare each of said first section and said plurality of sections to said second section; and an image subtraction device connected to said matching devices.

54. A system as recited in claim 53, comprising:

a relative area determination circuit connected to one of said image acquisition device and said image storage device.

55. A system as recited in claim 54, comprising:

a local matching circuit connected to said two-dimensional matching circuit.

56. A system as recited in claim 55, comprising:

a warping circuit connected to said local matching circuit.

57. A system as recited in claim 55, wherein said local matching circuit comprises a cross-correlation circuit.

58. A system as recited in claim 53, comprising:

a registration analysis circuit connected to said subtraction circuit.

59. A system as recited in claim 58, wherein said registration analysis circuit comprises:

a histogram analysis circuit;

an image data retrieval circuit connected to said histogram analysis circuit; and an image reconstruction circuit connected to said image data retrieval circuit.

* * * * *